(12) United States Patent
Sasisekharan et al.

(10) Patent No.: US 7,737,692 B2
(45) Date of Patent: Jun. 15, 2010

(54) METHOD FOR SEQUENCE DETERMINATION USING NMR

(75) Inventors: Ram Sasisekharan, Bedford, MA (US); Ganesh Venkataraman, Bedford, MA (US); Rahul Raman, Arlington, MA (US); Benito Casu, Milan (IT); Giangiacomo Torri, Milan (IT); Marco Guerrini, Varese (IT)

(73) Assignees: Massachusetts Institute of Technology, Cambridge, MA (US); Istituto di Ricerche Chimiche e Biochimiche G. Ronzoni, Milan (IT)

( * ) Notice: Subject to any disclaimer, the term of this patent is extended or adjusted under 35 U.S.C. 154(b) by 0 days.

(21) Appl. No.: 12/261,000

(22) Filed: Oct. 29, 2008

(65) Prior Publication Data

US 2009/0045811 A1    Feb. 19, 2009

Related U.S. Application Data

(63) Continuation of application No. 12/144,995, filed on Jun. 24, 2008, which is a continuation of application No. 10/441,970, filed on May 20, 2003, now Pat. No. 7,508,206.

(60) Provisional application No. 60/381,940, filed on May 20, 2002.

(51) Int. Cl.
*G01V 3/00* (2006.01)
(52) U.S. Cl. ...................... 324/309; 324/307
(58) Field of Classification Search ......... 324/300–322; 435/232, 252, 320, 325; 304/182; 530/811; 536/23; 702/27
See application file for complete search history.

(56) References Cited

U.S. PATENT DOCUMENTS

| 5,284,558 | A * | 2/1994 | Linhardt et al. ............. 204/451 |
| 6,190,522 | B1 | 2/2001 | Haro |
| 6,217,863 | B1 | 4/2001 | Godavarti et al. |
| 6,429,302 | B1 | 8/2002 | Kennedy |
| 6,597,996 | B1 | 7/2003 | Venkataraman et al. |
| 6,869,789 | B2 | 3/2005 | Liu et al. |
| 6,962,699 | B2 * | 11/2005 | Pojasek et al. ............. 424/94.5 |
| 7,056,504 | B1 | 6/2006 | Sasisekharan et al. |
| 7,083,937 | B2 | 8/2006 | Sasisekharan et al. |
| 7,105,334 | B2 * | 9/2006 | Pojasek et al. ............. 435/232 |

(Continued)

FOREIGN PATENT DOCUMENTS

JP         06-506830  A1      8/1994

(Continued)

OTHER PUBLICATIONS

Agrawal et. al.: Nuclear magnetic resonance spectroscopic approaches for the determination of interglycosidic linkage and sequence in oligosaccharides; Phytochemical Analysis Vol. 7, 113-13- (1996).*

(Continued)

*Primary Examiner*—Brij B Shrivastav
(74) *Attorney, Agent, or Firm*—Wolf, Greenfield & Sacks, P.C.

(57) ABSTRACT

The invention relates to methods for analyzing polysaccharides. In particular, compositional and sequence information about the polysaccharides are derived. Some methods use NMR in conjunction with another experimental method, such as, capillary electrophoretic techniques for the analysis.

38 Claims, 3 Drawing Sheets

U.S. PATENT DOCUMENTS

| | | | |
|---|---|---|---|
| 7,110,889 B2* | 9/2006 | Venkataraman et al. | 702/27 |
| 7,117,100 B2 | 10/2006 | Venkataraman et al. | |
| 7,129,335 B2* | 10/2006 | Pojasek et al. | 530/412 |
| 7,139,666 B2 | 11/2006 | Venkataraman et al. | |
| 7,247,445 B2 | 7/2007 | Sasisekharan et al. | |
| 7,270,815 B2 | 9/2007 | Sasisekharan et al. | |
| 7,317,091 B2 | 1/2008 | Lazar et al. | |
| 7,390,633 B2 | 6/2008 | Liu et al. | |
| 7,396,824 B2 | 7/2008 | Sasisekharan et al. | |
| 7,399,604 B2* | 7/2008 | Sasisekharan et al. | 435/13 |
| 7,407,810 B2 | 8/2008 | Raguram | |
| 7,412,332 B1* | 8/2008 | Venkataraman et al. | 702/19 |
| 7,429,474 B2 | 9/2008 | Sasisekharan et al. | |
| 7,455,986 B2 | 11/2008 | Liu et al. | |
| 7,504,247 B2 | 3/2009 | Sasisekharan et al. | |
| 7,507,570 B2* | 3/2009 | Prabhakar et al. | 435/232 |
| 7,508,206 B2 | 3/2009 | Sasisekharan et al. | |
| 7,541,806 B2* | 6/2009 | Appelt et al. | 324/303 |
| 7,553,950 B2 | 6/2009 | Prabhakar et al. | |
| 7,560,106 B2 | 7/2009 | Sasisekharan et al. | |
| 7,585,642 B2 | 9/2009 | Sasisekharan et al. | |
| 7,592,152 B2 | 9/2009 | Prabhakar et al. | |
| 2002/0122793 A1 | 9/2002 | Liu et al. | |
| 2002/0128225 A1 | 9/2002 | Liu et al. | |
| 2002/0169143 A1 | 11/2002 | Sasisekharan et al. | |
| 2002/0172961 A1 | 11/2002 | Schneider et al. | |
| 2003/0008326 A1 | 1/2003 | Sem et al. | |
| 2003/0008820 A1 | 1/2003 | Kwan et al. | |
| 2003/0099628 A1 | 5/2003 | Liu et al. | |
| 2003/0191587 A1 | 10/2003 | Venkataraman | |
| 2003/0203385 A1* | 10/2003 | Venkataraman et al. | 435/6 |
| 2004/0091471 A1 | 5/2004 | Myette et al. | |
| 2004/0091472 A1 | 5/2004 | Pojasek et al. | |
| 2004/0092037 A1 | 5/2004 | Sasisekharan et al. | |
| 2004/0197933 A1 | 10/2004 | Venkataraman et al. | |
| 2004/0204869 A1 | 10/2004 | Venkataraman et al. | |
| 2005/0037376 A1 | 2/2005 | Sasisekharan et al. | |
| 2005/0214276 A9 | 9/2005 | Myette et al. | |
| 2005/0227320 A1 | 10/2005 | Pojasek et al. | |
| 2005/0233401 A1 | 10/2005 | Liu et al. | |
| 2005/0233402 A1 | 10/2005 | Liu et al. | |
| 2005/0233419 A1 | 10/2005 | Pojasek et al. | |
| 2006/0024664 A1 | 2/2006 | Sasisekharan et al. | |
| 2006/0057638 A1 | 3/2006 | Bosques et al. | |
| 2006/0067927 A1 | 3/2006 | Chandrasekaran et al. | |
| 2006/0067928 A1 | 3/2006 | Liu et al. | |
| 2006/0078959 A1 | 4/2006 | Prabhakar et al. | |
| 2006/0083711 A1 | 4/2006 | Berry et al. | |
| 2006/0105430 A1 | 5/2006 | Sasisekharan et al. | |
| 2006/0127950 A1 | 6/2006 | Bosques et al. | |
| 2006/0154894 A1 | 7/2006 | Berry et al. | |
| 2006/0177885 A1 | 8/2006 | Myette et al. | |
| 2006/0177910 A1 | 8/2006 | Myette et al. | |
| 2006/0177911 A1 | 8/2006 | Myette et al. | |
| 2006/0182734 A1 | 8/2006 | Liu et al. | |
| 2006/0183713 A1 | 8/2006 | Liu et al. | |
| 2006/0183891 A1 | 8/2006 | Myette et al. | |
| 2006/0292130 A1 | 12/2006 | Sasisekharan et al. | |
| 2006/0292655 A1 | 12/2006 | Sasisekharan et al. | |
| 2006/0292673 A1 | 12/2006 | Sasisekharan et al. | |
| 2007/0004012 A1 | 1/2007 | Sasisekharan et al. | |
| 2007/0020243 A1 | 1/2007 | Sengupta et al. | |
| 2007/0065424 A1 | 3/2007 | Pojasek et al. | |
| 2007/0065921 A1 | 3/2007 | Sasisekharan et al. | |
| 2007/0066769 A1 | 3/2007 | Venkataraman et al. | |
| 2007/0134226 A1* | 6/2007 | Myette | 424/94.5 |
| 2007/0148157 A1 | 6/2007 | Prabhakar et al. | |
| 2007/0148158 A1 | 6/2007 | Sasisekharan et al. | |
| 2007/0148740 A1 | 6/2007 | Prabhakar et al. | |
| 2007/0161073 A1 | 7/2007 | Sasisekharan et al. | |
| 2007/0202563 A1 | 8/2007 | Prabhakar et al. | |
| 2007/0224670 A1 | 9/2007 | Prabhakar et al. | |
| 2008/0071148 A1 | 3/2008 | Bosques et al. | |
| 2008/0171375 A1* | 7/2008 | Myette | 435/232 |
| 2008/0278164 A1 | 11/2008 | Sasisekharan et al. | |
| 2008/0301178 A1 | 12/2008 | Venkataraman et al. | |
| 2009/0045811 A1 | 2/2009 | Sasisekharan et al. | |
| 2009/0081635 A1 | 3/2009 | Liu et al. | |
| 2009/0105463 A1 | 4/2009 | Berry et al. | |
| 2009/0119027 A1 | 5/2009 | Venkataraman et al. | |
| 2009/0156477 A1 | 6/2009 | Berry et al. | |
| 2009/0269326 A1* | 10/2009 | Myette et al. | 424/94.6 |
| 2009/0298157 A1* | 12/2009 | Myette | 435/232 |

FOREIGN PATENT DOCUMENTS

| | | |
|---|---|---|
| WO | WO 97/16556 A1 | 5/1997 |
| WO | WO 00/12726 A2 | 3/2000 |
| WO | WO 00/65521 A2 | 11/2000 |
| WO | WO 01/66772 A2 | 9/2001 |
| WO | WO 02/23190 A2 | 3/2002 |
| WO | WO 02/32406 A2 | 4/2002 |
| WO | WO 02/077199 A2 | 10/2002 |
| WO | WO 03/102160 A3 | 12/2003 |
| WO | WO 2004/055491 A2 | 7/2004 |
| WO | WO 2004/062592 A2 | 7/2004 |
| WO | WO 2004/069152 A2 | 8/2004 |
| WO | WO 2005/087920 A2 | 9/2005 |
| WO | WO 2005/110438 A2 | 11/2005 |
| WO | WO 2005/111627 A2 | 11/2005 |
| WO | WO 2006/076627 A2 | 7/2006 |
| WO | WO 2006/083328 A2 | 8/2006 |
| WO | WO 2006/088491 A2 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

Ferro et al., Determination of the composition of the oligosaccharide phosphate fraction of Pichia (Hansenula) holstii NRRL Y-2448 phosphomannan by capillary electrophoresis and HPLC. Carbohydr Res. Feb. 5, 2002;337(2):139-46.

Haslinger et al., Sequential analysis of oligosaccharide structures by modern NMR techniques. Liebigs Annalen Der Chemie. Jul. 1990;7:713-4.

Hisamatsu et al., Structural analysis of oligosaccharide by NMR and FAB-MS. Chemistry Organism. 1992;30(10):649-55.

La Ferla et al., Synthesis of disaccharidic sub-units of a new series of heparin related oligosaccharides. Tetrahedron; Aug. 6, 1999;55(32): 9867-80.

Mansson et al., Structural analysis of the lipopolysaccharide from nontypeable Haemophilus influenzae strain 1003. Eur J Biochem. Feb. 2002;269(3):808-18.

Matsuda, Structural studies on oligosaccaharides. Denkun kagaku [J Jap Soc Starch Sci]. 1981;28(2):100-8.

Nadanaka et al., The unusual tetrasaccharide sequence GlcA beta 1-3GalNAc(4-sulfate)beta 1-4GlcA(2-sulfate)beta 1-3GalNAc(6-sulfate) found in the hexasaccharides prepared by testicular hyaluronidase digestion of shark cartilage chondroitin sulfate D. Glycobiology. Mar. 1997;7(2):253-63.

Ojeda et al., Synthesis of heparin-like oligosaccharides on polymer supports. Glycoconj J. 2004;21(5):179-95.

Rudd et al., Oligosaccharide sequencing technology. Nature. Jul. 10, 1997;338(6638):205-7.

Toida et al., Structural analysis of heparan sulfate and heparan sulfate oligosaccharides. TIGG. 1998;10(52):125-36.

Venkataraman et al., Sequencing complex polysaccharides. Science. Oct. 15, 1999;286(5439):537-42.

* cited by examiner

METHOD FOR SEQUENCE DETERMINATION USING NMR

RELATED APPLICATIONS

This application is a continuation of U.S. patent application Ser. No. 12/144,995, filed Jun. 24, 2008, now pending, which is a continuation of U.S. patent application Ser. No. 10/441,970, filed May 20, 2003, allowed, which claims the benefit of U.S. provisional patent application No. 60/381,940 filed May 20, 2002 under 35 U.S.C. §119, the entire contents of each of which are incorporated herein by reference.

GOVERNMENT SUPPORT

This invention was made with government support under grant numbers GM57073 and CA090940 awarded by The National Institute of Health. The government has certain rights in the invention.

FIELD OF THE INVENTION

The invention relates to methods for analyzing compositional and sequence information of polysaccharides.

BACKGROUND OF THE INVENTION

Heparin and heparan sulfate glycosaminoglycans are complex acidic polysaccharides that are involved in a variety of physiological and pathological conditions. Advances in different areas of biology have elucidated the potential roles of HSGAGs in key biological processes (Casu and Lindahl, 2001; Lindahl, 2000; Sasisekharan and Venkataraman, 2000; Shriver et al., 2002) including thrombosis (Petitou et al., 1999), angiogenesis (Sasisekharan et al., 1997), viral invasion (Chen et al., 1997; Fry et al., 1999; Shukla et al., 1999) and tumor growth (Hulett et al., 1999; Vlodavsky et al., 1999; Liu et al. 2002). The repeat unit of a HSGAG polymer is a disaccharide comprising a uronic acid (U), which can exist in two different epimeric forms—α-L-iduronic (I) or β-D-glucuronic (G), linked 1→4 to a α-D-glucosamine residue (A). There are variations within the disaccharide unit in the form of sulfation at the 2-O position of the uronic acid, 3-O and 6-O position of the glucosamine and sulfation or acetylation of the N-position of the glucosamine (Casu and Lindahl, 2001).

Perhaps the best studied structure-activity relationships in HSGAGs is a pentasaccharide sequence in heparin that specifically binds to and activates antithrombin-III thereby playing an inhibitory role in the blood coagulation cascade (Bourin and Lindahl, 1993). Heparin and its derivatives, low molecular weight heparins (LMWHs), are the most widely used clinical agents for prevention of deep vein thrombosis after surgery (Breddin, 2000) and for prevention of myocardial infarction after coronary invasion procedures (Cohen, 1999). Based on the anticoagulant properties of heparin, new therapeutic applications of heparin are being envisaged (Rosenberg, 2001). A synthetic version of the pentasaccharide has been used as an antithrombotic drug (Turpie et al, 2001).

In order to understand the structure-activity relationship of HSGAGs, several analytical tools have been developed for sequencing oligosaccharides which include gel electrophoresis (Turnbull et al., 1999), HPLC (Vives et al., 1999), matrix assisted laser desorption/ionization mass spectrometry (MALDI-MS) (Venkataraman et al., 1999) and nanoelectrospray mass spectrometry (Pope et al., 2001). These analytical tools have been applied to dissect the HSGAG oligosaccharide into smaller fragments using a battery of depolymerizing enzymes and other chemical methods and determining the sequence of the oligosaccharides based on specific properties of the smaller fragments (Kreuger et al. 2001).

SUMMARY OF THE INVENTION

The invention relates, in part, to an analytical tool for analyzing oligosaccharides, such as HSGAGs. Determining the sequence and/or composition of an oligosaccharide is helpful for elucidating the structure-function relationship of oligosaccharides in key biological processes.

In some aspects, a method of determining the composition of an oligosaccharide is provided. The method involves obtaining a measurement of a first property of the oligosaccharide using NMR spectroscopy, and obtaining a measurement of a second property of the oligosaccharide by a second experimental method, wherein the first and second properties determine the composition. In one embodiment, the second property of the oligosaccharide is measured by capillary electrophoresis.

A method of analyzing an oligosaccharide is provided according to other aspects. The method involves obtaining a measurement of a first type of disaccharide linkage of the oligosaccharide by a first experimental method, and obtaining a measurement of a second type of disaccharide linkage of the oligosaccharide by a second experimental method, to analyze the oligosaccharide. In one embodiment the first type of disaccharide linkage is measured by NMR spectroscopy. In another embodiment the second type of disaccharide linkage is measured by capillary electrophoresis.

According to another aspect, a method of analyzing an oligosaccharide, by identifying a first property of the oligosaccharide by NMR spectroscopy, and identifying a second property of the oligosaccharide by capillary electrophoresis, to analyze the oligosaccharide is provided.

The methods, in some embodiments, involve determining possible sequences of the oligosaccharide that are consistent with the measurement from the NMR spectroscopy and second experimental method.

In other embodiments the methods involve constructing a list of possible sequences based on the measurement from the NMR spectroscopy, and eliminating sequences from the list of possible sequences that are not consistent with the measurement of the second experimental method.

The second experimental method may be used to distinguish the reducing and non-reducing ends of the oligosaccharide or fragments thereof. In one embodiment, the second experimental method includes chemical degradation. In another embodiment the second experimental method includes end-labeling.

The second experimental method may also be used to determine the signature of the reducing end of the oligosaccharide or fragments thereof. In one embodiment the signature of the reducing end is determined with capillary electrophoresis. The second experimental method may allow the determination of the sulfation pattern of the second type of disaccharide linkage.

The NMR spectroscopy, in some embodiments, includes the determination of the sulfation pattern of the oligosaccharide or fragments thereof. In another embodiment the NMR is performed to identify and quantify both reducing and non-reducing ends.

The methods may optionally involve obtaining a measure of an additional property of the oligosaccharide by a third experimental method to further eliminate sequences not consistent with measurements obtained from the third experimental method.

In some embodiments the NMR spectroscopy is 1D proton or 2D COSY/TOCSY. In other embodiments, the NMR spectroscopy is HSQC, DQF-COSY, NOESY or ROESY. The NMR spectroscopy may also be any combination of the above.

The NMR spectroscopy may be performed on the oligosaccharide in its intact form. Alternatively, it may be performed on the oligosaccharide in a fragmented form. The fragmented form may be produced by enzymatic digestion. Enzymatic digestions may be complete or, in the alternative, partial.

The second experimental method may also involve digesting the oligosaccharide to a fragmented form, e.g., optionally produced by enzymatic digestion. In one embodiment the enzymatic digestion is complete.

In another aspect, a method of generating a list of possible sequences of an oligosaccharide is provided. The method involves defining a set of properties of the oligosaccharide by performing NMR spectroscopy and a second experimental method, wherein the NMR spectroscopy provides a measurement of a first type of disaccharide linkage and the second experimental method provides a measurement of a second type of disaccharide linkage, and constructing a list of possible sequences based on the set of properties of the oligosaccharide. In one embodiment the NMR spectroscopy includes a measure of the monosaccharide composition of the oligosaccharide.

The method may involve a data structure which represents the properties as non-character values. In one embodiment the data structure includes a value for each type of monosaccharide. In another embodiment the data structure encodes a value for each type of disaccharide linkage. In another embodiment the values are binary.

A list of possible sequences of an oligosaccharide produced from the methods is also provided.

In the above aspects and embodiments the labels of "first" and "second" experimental methods are not intended to denote the order in which the experiments need be performed. In some embodiments, the NMR spectroscopy may be performed before the other experimental methods, while in other embodiments, the NMR spectroscopy may be performed after the other method. In still other embodiments the two or more experimental methods may be performed concurrently.

Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF THE DRAWINGS

FIG. 1 is a representation of the (A) disaccharide building block of heparin and heparan sulfate polysaccharides (left) with positions of sulfation marked as X (Y position can be sulfated or acetylated). The hexadecimal code (middle) to represent the disaccharide repeat unit in the PEN framework was described in our previous study (Venkataraman et al., 1999). The decomposition of the disaccharide hexadecimal code to a base$_4$ code for the uronic acid and base$_8$ (octal) code for the glucosamine is shown on in (B) The base$_4$ codes for the (i) uronic acids, (ii) octal codes for glucosamines, (iii) signed hexadecimal codes for A-U linkages and (iv) ΔU-A linkages observed in the oligosaccharides used in this study.

FIG. 2 shows the (A) $^1$H 500 MHz spectrum of synthetic pentasaccharide P1. (B) $^1$H 500 MHz spectrum of synthetic pentasaccharide P2. Characteristic proton chemical shifts of the constituent monosaccharides are marked accordingly.

FIG. 3 illustrates the $^1$H 500 MHz spectra of H10 decasaccharide (A). The line broadening is due to the presence of paramagnetic impurity; addition of deuterated EDTA provides a better resolved spectrum (B). The anomeric region expansion with the signals assignment is shown in (C).

DETAILED DESCRIPTION

Heparin and heparan sulfate glycosaminoglycans (HS-GAGs) are cell surface polysaccharides that bind to a multitude of signaling molecules, enzymes, pathogens and modulate critical biological processes ranging from cell growth and development to anticoagulation and viral invasion. Heparin has been widely used as anticoagulant in a variety of clinical applications for several decades. The heterogeneity and complexity of HSGAGs pose significant challenges to their purification and characterization of structure-function relationship.

Several analytical techniques including gel electrophoresis, chromatography and mass spectrometry have been successfully applied to sequence small amounts of HSGAG oligosaccharides. The prerequisite for the success of most of these techniques is predictable and controlled depolymerization of HSGAG oligosaccharide into smaller fragments using a combination of enzymatic and chemical degradation methods. Importantly, for some of the sequencing strategies, the use of multiple exo-enzymes are required to accurately determine the different modifications of the disaccharide units.

A methodology was developed that utilizes experimental methods to characterize oligosaccharides. The invention, relates in some aspects to a method for analyzing an oligosaccharide, such as an HSGAG. These methods, in some embodiments, encompass determining the presence or identity of an oligosaccharide in a sample through the analysis of the oligosaccharide. In other embodiments, methods for assessing the purity of an oligosaccharide in a sample are provided. The term "analyzing" as used herein refers to the identification of one or more properties of an oligosaccharide. In some instances the analysis may be extensive and provide considerable information about the composition of an oligosaccharide. The term analyzing can encompass sequencing an oligosaccharide or determining the composition of an oligosaccharide. The term "determine the composition" refers to the identification of enough properties of an oligosaccharide that the oligosaccharide can be distinguished from other oligosaccharides. When the information regarding the properties is compiled using the numerical PEN framework derived by the instant inventors the sequence of an oligosaccharide, including order of building blocks and linkage information, can be compiled.

The analysis of the oligosaccharide may involve identification of monomeric properties and linkage information. The importance of identifying the types of linkages between monosaccharides and disaccharides of oligosaccharides can be illustrated using HSGAGs as an example. The repeat unit of a HSGAG polymer is a disaccharide comprising a uronic acid (U), which can exist in two different epimeric forms—α-L-iduronic (I) of β-D-glucuronic (G), linked 1→4 to a α-glucosamine residue (A). There are variations within the disaccharide unit in the form of sulfation or acetylation of the N-position of the glucosamine. Characteristic proton and $^{13}$C chemical shifts have been identified for commonly occurring monosaccharides and heparin and the relative abundance of these monosaccharides can be quantitatively determined by integrating the proton signals. In addition to characterization of the monosaccharides, the anomeric proton signals of the glucosamines can be resolved further to identify linkage information regarding the neighboring uronic acid (A-U linkage) with a defined epimeric and sulfation state.

The composition of an oligosaccharide can be determined by the methods described herein using two or more experimental techniques to measure properties of the oligosaccharide. One of the experimental techniques is nuclear magnetic resonance (NMR). By utilizing NMR the number of experimental constraints required to sequence HSGAG oligosaccharides can be reduced. The NMR can be utilized with at least one other type of experimental technique. It has been demonstrated herein that the integration of NMR and capillary electrophoresis (CE) data sets with the help of the PEN framework can reduce the need for NOESY/ROESY experiments which may require a lot more sample and more sophisticated instruments for reasonable sensitivity.

Thus, methods are provided to analyze the oligosaccharides to determine the sequence of the oligosaccharide. Using a numerical PEN framework, the information derived from the compositional analysis, e.g., two distinct linkage data sets, can be compiled to construct the sequence in a rapid, systematic and unbiased fashion. The numerical nature of the PEN framework facilitates moving between monosaccharide, disaccharide U-A and A-U linkage information using simple mathematical operations thus facilitating a systematic and unbiased way of rapidly arriving at a HSGAG sequence.

The examples discussed below demonstrate the use of the methodology and the computational approach described herein. Examples 1 and 2 describe pentasaccharides containing both $I_{2S}$ and G. These examples demonstrate the value of determining the signature of the reducing end (methylation) for application of the analytical methods described herein. Once all of the A-U and U-A linkages are determined, the knowledge of the reducing or non-reducing end enables the determination of the sequence by moving forward or backward. Decasaccharide H10 is one of the most complex decasaccharides that has been characterized and verified using a combination of analytical tools.

Example 3 highlights the strengths of the methods described herein in comparison with other analytical tools that have been used for characterization of H10 in the past. Earlier sequencing approaches for this decasaccharide required numerous steps. Using the methods described herein we arrived at the sequence of H10 in an unbiased fashion by obtaining two distinct sets of A-U and U-A linkage information that were quantitatively determined using a minimal set of experimental data. This example illustrates the flexibility of the computational method to construct a list of all possible combinations of sequences satisfying the linkage and monosaccharide composition obtained from NMR data and elimination of sequences that did not satisfy the CE data.

Thus, the list of possible sequences can be constructed based on the identified properties, such as the charge, the nature and number of units of the oligosaccharide, the nature and number of chemical substituents on the units, disaccharide linkage, reducing and non-reducing ends, and the stereospecificity of the oligosaccharide, which reveal information about the building blocks of the oligosaccharide determined from the measurements of an experimental method.

The structural properties of oligosaccharides may provide useful information about the function of the oligosaccharide. For instance, the properties of the oligosaccharide may reveal the entire sequence of units of the oligosaccharide, which is useful for identifying the oligosaccharide. Similarly, if the sequence of the oligosaccharide was previously unknown, the structural properties of the oligosaccharide are useful for comparing the oligosaccharide to known oligosaccharides having known functions. The properties of the oligosaccharide may also reveal that a oligosaccharide has a net charge or has regions which are charged. This information is useful for identifying compounds that the oligosaccharide may interact with or predicting which regions of a oligosaccharide may be involved in a binding interaction or have a specific function.

The invention is useful for identifying properties of oligosaccharides. A "property" as used herein is a characteristic (e.g., structural characteristic) of the oligosaccharide that provides information (e.g., structural information) about the oligosaccharide. A compilation of several properties of a oligosaccharide may provide sufficient information to identify a chemical unit or even the entire oligosaccharide but the property of the oligosaccharide itself does not encompass the chemical basis of the chemical unit or oligosaccharide. Due to the complexity of the oligosaccharide, a property may identify a type of monomeric building block of the oligosaccharide. The units of the oligosaccharides have more variables in addition to its basic chemical structure. For example, the oligosaccharide may be acetylated or sulfated at several sites on the building block, or it may be charged or uncharged. Thus, one property of an oligosaccharide may be the identity of one or more basic building blocks of the oligosaccharides.

A basic building block alone, however, may not provide information about the charge and the nature of substituents of the saccharide or disaccharide. For example, a building block of uronic acid may be iduronic or glucuronic acid. Each of these building blocks may have additional substituents that add complexity to the structure of the building block. A single property, however, may not identify such additional substitutes charges, etc., in addition to identifying a complete building block of a oligosaccharide. This information, however, may be assembled from several properties. Thus, a property of an oligosaccharide as used herein encompasses a monosaccharide or disaccharide building block of an oligosaccharide. The NMR methods described herein are useful for identifying information about basic monosaccharide building blocks.

The type of property that will provide structural information about the oligosaccharide is a property such as charge, molecular weight, nature and degree of sulfation or acetylation, or type of saccharide. Properties include but are not limited to charge, chirality, nature of substituents, quantity of substituents, molecular weight, molecular length, compositional ratios of substituents or units, type of basic building block of a oligosaccharide, hydrophobicity, enzymatic sensitivity, hydrophilicity, secondary structure and conformation (i.e., position of helices), spatial distribution of substituents, ratio of one set of modifications to another set of modifications (i.e., relative amounts of 2-O sulfation to N-sulfation or ratio of iduronic acid to glucuronic acid), binding sites for proteins, and linkage information. Other properties will easily be identified by those of ordinary skill in the art. A substituent, as used herein is an atom or group of atoms that substitute a unit, but are not themselves the units.

It has been discovered that the use of NMR can significantly reduce the number of experimental constraints required to derive enough property information to identify a complete sequence of an oligosaccharide. By providing information regarding specific linkages and monosaccharide compositions NMR dramatically improves sequencing techniques.

Thus, one embodiment of the methods utilizes the strengths of NMR to measure A-U linkages and an orthogonal set of U-A linkage information obtained from CE to construct the sequence of an oligosaccharide. NMR is a powerful tool that can be used to determine numerous parameters defining the sequence of an intact oligosaccharide including monosaccharide composition, sulfation pattern and linkage between glucosamine and uronic acid (A-U). These parameters can be readily determined independent of sequence length and variability of building blocks, using a single series of simple 1D proton and 2D COSY/TOCSY experiments. Thus, by combining the distinct linkage information between adjacent monosaccharides obtained from NMR (A-U linkage information) with the U-A linkage information obtained from a single capillary electrophoresis experiment to rapidly arrive at the sequence of HSGAG oligosaccharides.

Interpretation of NMR spectra of HSGAGs, in the past, has had certain limitations due to overlaps in proton signals and absence of measurable coupling constants. Also the sensitivity of this technique is lower than those based on detection of chromatographic effluents (Turnbull et al, 1999; Vives et al, 1999; Kreuger et al, 2001) and on mass spectrometry (Pope et al., 2001; Venkataraman et al., 1999). Thus, it was very difficult to characterize samples that are only available in small quantities. It has been discovered that despite these limitations NMR can provide powerful analytical information useful in sequencing.

NMR spectroscopy is an analytical tool that allows for the determination of molecular structure. Utilizing the magnetic properties of some nuclei, the nuclear spins of the nuclei can be oriented randomly with an external magnetic field. Oriented nuclei that are subsequently irradiated at the correct frequency will absorb energy and transition to a higher energy state. Upon relaxation this energy is emitted and detected in various NMR systems. This irradiation of the nuclei occur in pulses. In basic one dimensional (1D) NMR the excitation is produced from a single pulse and emitted radiation is detected as free induction decay (FID). In two dimensional (2D) NMR spectroscopy the nuclei is irradiated with two pulses, and acquisition of the FID occurs at many time points with a delay between the pulses.

There are many types of 2D spectroscopy which include: COSY, TOSCY, NOESY and ROESY. COSY (Correlated Spectroscopy) is helpful in determining the energy that is arising from neighboring protons. This is helpful if there is overlap or second order coupling. Spin-spin coupling in COSY allows the spectrum to yield through bond interactions. Another 2D NMR technique capable of measuring through bond interactions is TOSCY (Total Correlated Spectroscopy) which identifies the protons that produce signals within a spin system. COSY and TOSCY can be combined for a more powerful structural analysis.

Other 2D NMR techniques allows the measurement of through space interactions. These methods are referred to as NOESY (Nuclear Overhauser Effect Spectroscopy) and ROESY (Rotational Nuclear Overhauser Effect Spectroscopy). NOESY identifies the signals emitted from protons that are close in space by not directly connected by bonding. The NOESY spectra give through space correlations as the change in intensity of multiplets from neighboring nuclei upon irradiation can be extensively measured. In instances where NOESY signals are weak, ROESY can be used, a similar technique that has cross peaks that are only negative. Other techniques may be used and would be apparent to those of ordinary skill in the art.

The NMR spectroscopy useful in the methods described herein may be 1D proton or 2D COSY/TOCSY in some embodiments. 1D proton NMR and 2D COSY/TOCSY NMR spectra provide quantitative information on multiple parameters including monosaccharide composition, sulfation states and A-U linkage information that define the sequence of an oligosaccharide. Furthermore, NMR provides an accurate method for direct quantification of the iduronic and glucuronic acid content in a sequence.

In the method of capillary gel-electrophoresis, reaction samples may be analyzed by small-diameter, gel-filled capillaries. The small diameter of the capillaries (50 µm) allows for efficient dissipation of heat generated during electrophoresis. Thus, high field strengths can be used without excessive Joule heating (400 V/m), lowering the separation time to about 20 minutes per reaction run, therefor increasing resolution over conventional gel electrophoresis. Additionally, many capillaries may be analyzed in parallel, allowing amplification of generated oligosaccharide information.

Currently, saccharide fragments are detected in capillary electrophoresis by monitoring at 232 nm, the wavelength at which the $\Delta^{4,5}$ double bond, generated upon heparinase cleavage, absorbs. However, other detection methods are possible. First, nitrous acid cleavage of heparin fragments, followed by reduction with $^3$H-sodium borohydride yields degraded fragments having a $^3$H radioactive tag. This represents both a tag which may be followed by capillary electrophoresis (counting radioactivity) or mass spectrometry (by the increase in mass). Another method of using radioactivity would be to label the heparin fragment with $S^{35}$. Similar to the types of detection possible for $^3$H-labeled fragments, $S^{35}$ labeled fragments may be useful for radioactive detection (CE) or measurement of mass differences (MS).

Especially in the case of $S^{35}$, this detection will be powerful. In this case, the human sulfotransferases may be used to label specifically a certain residue. This will give additional structural information.

Nitrous acid degraded fragments, unlike heparinase-derived fragments, do not have a UV-absorbing chromophore. For CE, two methods may be used to monitor fragments that lack a suitable chromophore. First is indirect detection of fragments. We may detect heparin fragments with our CE methodology using a suitable background absorber, e.g., 1,5-naphthalenedisulfonic acid. The second method for detection involves chelation of metal ions by saccharides. The saccharide-metal complexes may be detected using UV-V is just like monitoring the unsaturated double bond.

For determining the reducing or non-reducing ends a variety of experimental methods may be used including chemical degradation, end-labeling and capillary electrophoresis. In some embodiments, the ends may be determined by measuring a signature of a reducing or non-reducing end. For some oligosaccharides, the signature of the reducing end is methylation, and this signature may also be determined by capillary electrophoresis as well as other methods known in the art.

The reducing end of an oligosaccharide may be distinguished from the non-reducing end using mass tags, for instance. All of these tags involve selective chemistry with the anomeric OH (present at the reducing end of the oligosaccharide), thus labeling occurs at the reducing end of the chain. One common tag is 2-aminobenzoic acid which is fluorescent. In general tags involve chemistry of the following types: (1) reaction of amines with the anomeric position to form imines (i.e., 2-aminobenzoic acid), hydrazine reaction to form hydrazones, and reaction of semicarbazones with the anomeric OH to form semicarbazides. Commonly used tags (other than 2-aminobenzoic acid) include the following compounds:

1. semicarbazide

2. Girard's P reagent

3. Girard's T reagent 4. p-aminobenzoic ethyl ester 5. biotin-x-hydrazide 6. 2-aminobenzamide 7. 2-aminopyridine 8. anthranilic acid 9. 5-[(4,6-dichlorotriazine-2-yl)amino]-fluorescein 10. 8-aminonaphthalene-1,3,6-trisulfonic acid 11. 2-aminoacridone The properties, in some aspects of the invention, may be determined for the oligosaccharide in its intact or a fragmented form. Fragments of oligosaccharides in some embodiments of the invention can be produced by enzymatic digestion. In some embodiments the digestion is complete, or it may be a partial digestion.

Oligosaccharide fragments may be degraded using enzymes such as heparin lyase enzymes or nitrous acid and they may also be modified using different enzymes that transfer sulfate groups to the positions mentioned earlier or remove the sulfate groups from those positions. The modifying enzymes are exolytic and non-processive which means that they just act once on the non-reducing end and will let go of the heparin chain without sequentially modifying the rest of the chain. For each of the modifiable positions in the disaccharide unit there exits a modifying enzyme. An enzyme that adds a sulfate group is called a sulfotransferase, and an enzyme that removes a sulfate group is called a sulfatase. The modifying enzymes include 2-O sulfatase/sulfotransferase, 3-O sulfatase/sulfotransferase, 6-O sulfatase/sulfotransferase and N-deacetylase-N-sulfotransferase. The function of these enzymes is evident from their names, for example a 2-O sulfotransferase transfers a sulfate group to the 2-O position of an iduronic acid (2-O sulfated glucuronic acid is a rare occurrence in the HSGAG chains) and a 2-O sulfatase removes the sulfate group from the 2-O position of an iduronic acid.

HSGAG degrading enzymes include heparinase-I, heparinase-II, heparinase-III, D-glucuronidase and L-iduronidase. The heparinases cleave at the glycosidic linkage before a uronic acid. Heparinase I clips at a glycosidic linkage before a 2-O sulfated iduronic acid. Heparinase —III cleaves at a glycosidic linkage before an unsulfated glucuronic acid. Heparinase —II cleaves at both Hep-I and Hep-III cleavable sites. After cleavage by the heparinases the uronic acid before which the cleavage occurs loses the information of iduronic vs. glucuronic acid because a double bond is created between the C4 and C5 atoms of the uronic acid.

Glucuronidase and iduronidase, as their name suggests cleave at the glycosidic linkage after a glucuronic acid and iduronic acid respectively. Nitrous acid clips randomly at glycosidic linkages after a N-sulfated hexosamine and converts the six membered hexosamine ring to a 5 membered anhydromannitol ring.

As used herein, the term "oligosaccharide" is used interchangeably with the term "polysaccharide". An "oligosaccharide" is a biopolymer comprised of linked saccharide or sugar units. As used herein with respect to linked units of a oligosaccharide, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the chemical units of a particular oligosaccharide, are most common. Natural linkages include, for instance, amide, ester and thioester linkages. The units of an oligosaccharide analyzed by the methods of the invention may be linked, however, by synthetic or modified linkages. Oligosaccharides where the units are linked by covalent bonds will be most common but also include hydrogen bonded, etc.

The oligosaccharide is made up of a plurality of chemical units. A "chemical unit" as used herein is a building block or monomer which may be linked directly or indirectly to other building blocks or monomers to form an oligosaccharide. The oligosaccharide preferably is a oligosaccharide of at least two different linked units. An oligosaccharide is a biopolymer composed of monosaccharides linked to one another. In many oligosaccharides the basic building block of the oligosaccharide is actually a disaccharide unit which may be repeating or non-repeating. Thus, a unit when used with respect to a oligosaccharide refers to a basic building block of an oligosaccharide and may include a monomeric building block (monosaccharide) or a dimeric building block (disaccharide).

A "plurality of chemical units" is at least two units linked to one another. The oligosaccharides may be native or naturally-occurring oligosaccharides which occur in nature or non-naturally occurring oligosaccharides which do not exist in nature. The oligosaccharides typically include at least a portion of a naturally occurring oligosaccharide. The oligosaccharides may be isolated or synthesized de novo. For example, the oligosaccharides may be isolated from natural sources e.g. purified, as by cleavage and gel separation or may be synthesized e.g., by chemical synthesis.

A data structure for representing the properties of the oligosaccharide is also provided. In some embodiments the data structure represents the properties as non-character values. These values in some embodiments can be a binary value. In some embodiments the building blocks are the types of monosaccharides and disaccharide linkages of the oligosaccharide.

The rapid sequencing methodology for polysaccharides using chemical and enzymatic tools followed by numerical analysis techniques is described in detail in Venkataraman, G., et al., *Science,* 286, 537-542 (1999), and U.S. patent application Ser. Nos. 09/557,997 and 09/558,137, both filed on Apr. 24, 2000 and having common inventorship, all of which are specifically incorporated by reference.

EXAMPLES

Materials and Methods

The synthetic pentasaccharides P1 and P2 corresponding to the active sequence of heparin for AT-III binding were a gift from M. Petitou, Sanofi-Synthelabo, Toulouse, France. The decasaccharide H10, kindly provided by R. J. Linhardt (University of Iowa), was obtained by fractionation of heparinase digest of pig mucosal heparin, on an AT-III column as described earlier (Toida et al., 1996)

NMR Spectroscopy:

The oligosaccharide samples were prepared by dissolving 2 mg of the pentasaccharide and 150 μg of H10 in 0.5 ml of $D_2O$ 99.99%. Due to signal broadening caused by paramagnetic ions in H10, deuterated EDTA was added to the sample to remove these ions. (Neville et al., 1989) The $^1$H-NMR spectra were recorded at 500 MHz on a Bruker AMX 500 spectrometer at 60° C. with presaturation of the residual water signals and with recycle delay of 12 seconds; a 45° pulse was used. 2D DQF-COSY (Double Quantum Filtered-COSY) and TOCSY were measured in phase-sensitive mode using TPPI (Time Proportional Phase Incrementation), and a shifted square sine-bell function was applied before Fourier transformation. 32 and 512 scans for each FID were used for the pentasaccharide and the decasaccharide, respectively.

Compositional Analysis Using Capillary Electrophoresis (CE):

Compositional analysis of the oligosaccharides was completed by exhaustive enzymatic digest of a 30 μM sample followed by capillary electrophoresis (CE) as described earlier (Venkataraman et al., 1999). Briefly, to 1 nmol of oligosaccharide was added 200 nM of heparinases I, II, and III in 25 mM sodium acetate, 100 mM NaCl, 5 mM calcium acetate buffer, pH 7.0. The reaction was allowed to proceed at 30° C. overnight and then analyzed by CE in reverse polarity with a running buffer of 50 mM Tris/phosphate/10 μM dextran sulfate, pH 2.5.

Figure 1A:
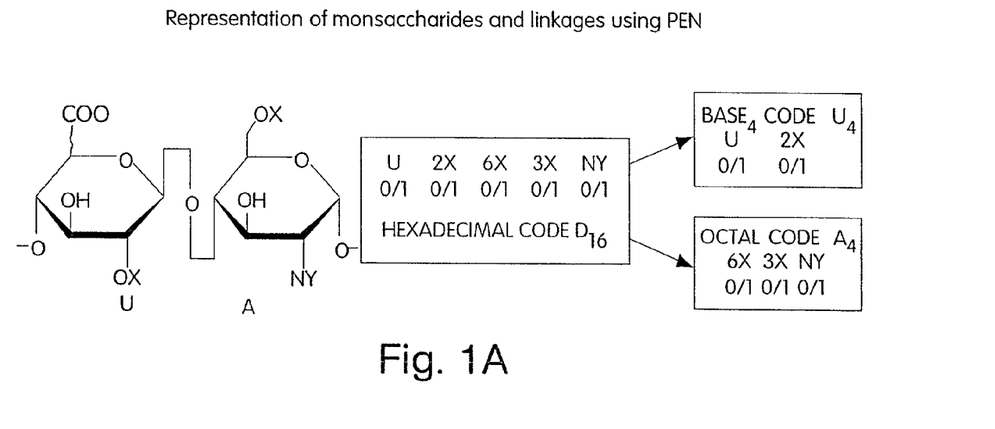
Figure 1B:
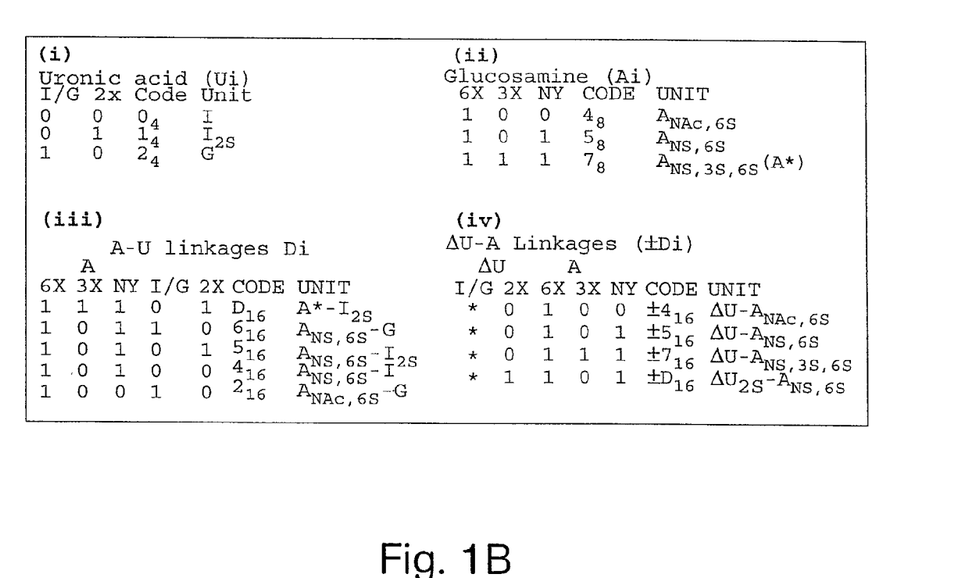

Incorporating CE and NMR Data as Constraints Using Pen Framework:

The PEN is a numerical notation scheme that encodes the sulfation pattern of a disaccharide building block as a series of binary on/off states and epimerization of the uronic acid as a + or – sign bit leading to a signed hexadecimal coding scheme (Venkataraman et al., 1999). Although, the PEN framework was originally developed to encode a U-A disaccharide building block (Di), it was mathematically decomposed into a $base_4$ code for representing the uronic acid monosaccharide (U) and a $base_8$ code for representing the glucosamine monosaccharide (A) (FIG. 1). Note that for the ΔU-A linkages the * used in the G/I position indicates that the epimeric state of the uronic acid is undetermined. It is also important to note that the signed hexadecimal codes representing the A-U linkages involves rearrangement of the 3 binary digits encoding A and two binary digits encoding U from the original PEN framework. As a result of the rearrangement, the + and – sign is used to represent 6-O sulfation (where + represents unsulfated and – represents sulfated) of the glucosamine instead of the epimeric state of the uronic acid since the 6-O sulfation is in the left most position of the A-U disaccharide code. Therefore there is no "extra" binary digit that has been added for representing the A-U disaccharide and we still use the signed $base_{16}$ hexadecimal code. Further the PEN framework was also used to encode an A-U disaccharide unit (Di') by transposing the 3 bits that encode for the sulfation state of the glucosamine with the 2 bits that encode the epimeric and sulfation state of the uronic acid (Table 1). The information obtained from NMR and CE data is shown in A. Columns 1-3 indicate the number of linkages between glucosamine residues (colored in gray) the uronic acids in column 4 obtained from NMR data. Columns 5-7 indicate the linkages between uronic acid and the glucosamines obtained from CE data. The sequences that satisfy the monosaccharide composition and A-U linkage information (Di') are shown in B. Application of the U-A linkages from CE data reduces $L_{NMR}$ to the final correct sequence.

TABLE 1

Sequence assignment of H10

A

| Linkage information from CE and NMR | | | | | | |
|---|---|---|---|---|---|---|
| A-U linkage from NMR | | | | U-A linkage from CE | | |
| A* | $A_{NAc, 6X}$ | $A_{NS, 6X}$ | | $A_{NS, 6S}$ | $A_{NAc, 6S}$ | A* |
| | | | $ΔU_{2S}$ | 3 | | |
| | | 2 | $I_{2S}$ | | | |
| | | 1 | I | | 1 | |
| 1 | | | G | | | 1 |

B

Sequences satisfying NMR data ($L_{NMR}$)

| | Di' linkage arrangement | | | | | Sequence |
|---|---|---|---|---|---|---|
| ΔU | -5 | -5 | -2 | -4 | A* | ±DDC-57 |
| ΔU | -5 | -5 | -5 | -2 | A* | ±DDD4-7 |
| ΔU | -5 | -2 | -5 | -4 | A* | ±DC-5D7 |
| ΔU | -5 | -4 | D | -2 | A* | ±DD5C-7 |
| ΔU | -5 | -2 | -4 | -5 | A* | ±DC-5DF |
| ΔU | -5 | -4 | -2 | -5 | A* | ±DD4-5F |
| ΔU | -2 | -5 | -5 | -4 | A* | ±C-5DD7 |
| ΔU | -4 | -5 | -5 | -2 | A* | ±D5DC-7 |
| ΔU | -2 | -5 | -4 | -5 | A* | ±C-5D5F |
| ΔU | -4 | -5 | -2 | -5 | A* | ±D5C-5F |
| ΔU | -2 | -4 | -5 | -5 | A* | ±C-55DF |

Apply CE data as constraints → Sequences satisfying CE and NMR Data ($L_{NMR,CE}$)

1-D proton NMR spectrum along with the 2D COSY, HSQC (Heteronuclear Single Quantum Coherence) and TOCSY spectra provide data on the chemical shifts and coupling constants of most the ring protons of the constituent monosaccharides. This data was used to uniquely identify the monosaccharides (Ui and Ai) and obtain the number of monosaccharides for a given length of the sequence. In addition to the identity of the glucosamine monosaccharides, their characteristic anomeric chemical shifts were further resolved to identify their linkages to adjacent uronic acids (Ai-Ui linkages defining Di' disaccharides). The Ui, Ai and Di' information was used to build a list of all the possible sequences satisfying this data ($L_{NMR}$). The sequences in $L_{NMR}$ represent a comprehensive sample space without any bias towards commonly occurring sequences.

Disaccharide compositional analysis using CE provides accurate information on the sulfation pattern of a ΔU-A disaccharide, thus identifying all the U-A linkages (±Di) whose sign bit is not known due to the $Δ^{4-5}$ unsaturated bond. Incorporating the disaccharide linkages ±Di obtained from CE data eliminates most of the sequences from $L_{NMR}$ converging on a single sequence.

Results

Example 1

Pentasaccharide P1

Figure 2A:
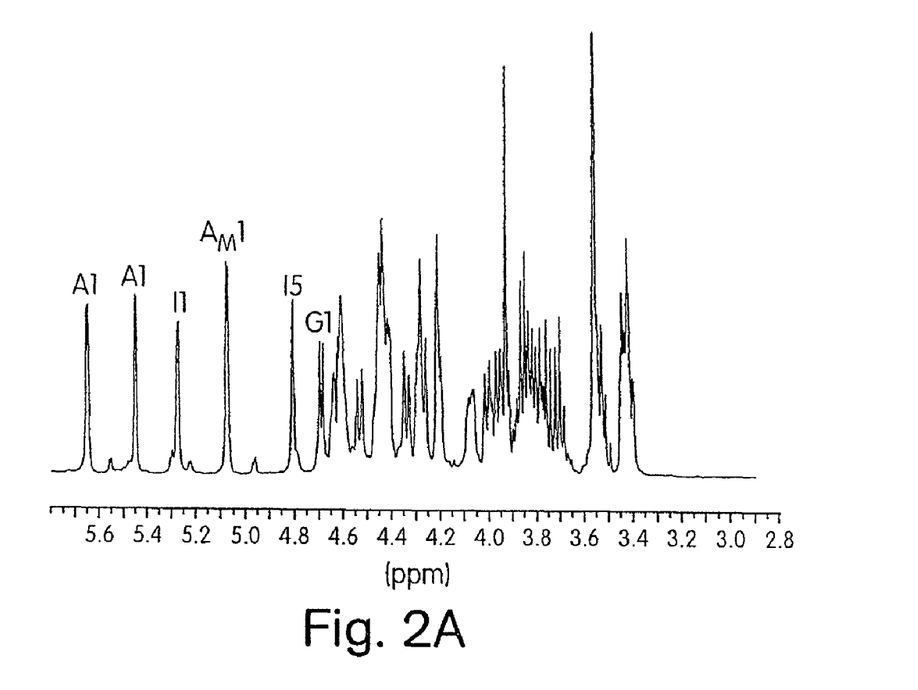

Several characteristic chemical shifts of the monosaccharide anomeric protons were observed in the 1D proton NMR spectrum of the pentasaccharide (FIG. 2A). The 1D proton signals along with the 2D COSY and TOCSY spectra were used to assign the monosaccharides. The signal patterns at 5.648, 5.438 and 5.041 ppm were assigned to the anomeric protons of N-sulfated glucosamines ($A_{NS,6X}$). Further, the 6-O sulfation of all these glucosamines were confirmed by TOCSY. The signal at 3.43/57.5 ppm indicates the presence of an O-methyl group linked to the reducing terminal. In addition, the presence of the methyl group at the reducing end also accounts for the absence of the typical reducing end carbon chemical shift (92-93 ppm). The chemical shifts at 5.251 and 4.635 are in agreement with an $I_{2S}$ and G respectively. The anomeric proton signals at 5.648 and 5.438 are distinguished further as arising from $A_{NS,6S}$-$I_{2S}$ and $A_{NS,6S}$-G respectively.

Integration of these peaks (Guerrini et al., 2001) gave the relative molar abundance of the glucosamines as $A_{NS,6S}$-$I_{2S}$: $A_{NS,6S}$-G:$A_{NS,6S}$=1:1:1 and that of the uronic acids as $I_{2S}$: G=1:1. Thus from the 1D and 2D NMR data the identity $A_i$=[$5_8$; $5_8$; $5_8$ ($A_{NS,6S}$)], $U_i$=[$1_4$ ($I_{2S}$); $2_4$ (G)] and relative abundance (m5=3, n1=n2=1) of the monosaccharides constituting the sequence were determined. Further the linkages Di'=[$-5_{16}$ ($A_{NS,6S}$-$I_{2S}$); $-6_{16}$ ($A_{NS,6S}$-G)] were also obtained form NMR data. Based on this information from the NMR data there can be two possible ($L_{NMR}$) pentasaccharide sequences: $5_8$ $1_4$ $5_8$ $2_4$ $5_8$ ($A_{NS,6S}$-$I_{2S}$-$A_{NS,6S}$-G-$A_{NS,6S,OMe}$) and $5_8$ $2_4$ $5_8$ $1_4$ $5_8$ ($A_{NS,6S}$-G-$A_{NS,6S}$-$I_{2S}$-$A_{NS,6S,OMe}$).

Capillary electrophoresis of the fragments formed by complete digestion of the pentasaccharide with the heparinases resulted in two peaks corresponding to a trisulfated $\Delta U_{2S}A_{NS,6S}$ and a disulfated disaccharide $\Delta UA_{NS,6S}$ thus defining ±Di= [$D_{16}$; ±$5_{16}$]. The relative molar abundance of these two disaccharides was calculated as 1:1 by integration of the CE signals and normalizing the peak areas using an internal calibration. The migration time of the ±$D_{16}$ disaccharide was slightly different from the standard indicating that the methylated glucosamine is a part of the trisulfated ±$D_{16}$ disaccharide. Thus the data from CE fixes the sulfation state of methylated reducing end disaccharide. Incorporating the constraints from CE data eliminated one of the sequences from $L_{NMR}$ thus converging on $5_8$ $2_4$ $5_8$ $1_4$ $5_8$ ($A_{NS,6S}$-G-$A_{NS,6S}$-$I_{2S}$-$A_{NS,6S,OMe}$).

Example 2

Pentasaccharide (P2)

Figure 2B:
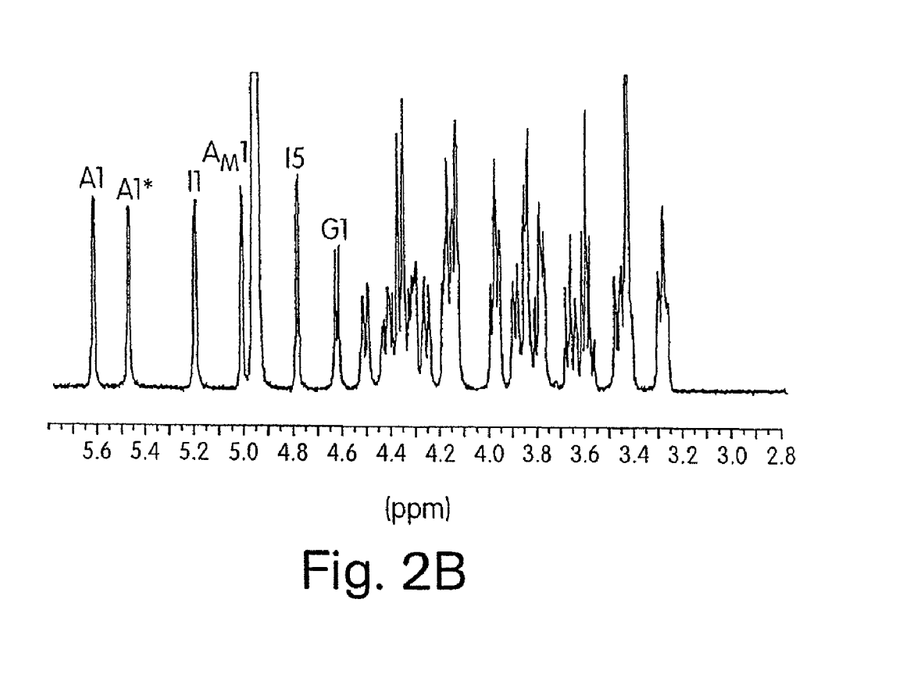

From the 1D proton spectrum (FIG. 2B) the signal pattern (anomeric peaks at 5.64/99.6 ppm, 5.50/98.1 ppm) is consistent with N-sulfated, 6-O-sulfated glucosamines ($A_{NS,6S}$), and A* bearing an extra 3-O sulfate group. Similar to Example 1, the signal pattern at 3.43/57.5 ppm corresponds to a glucosamine with a methylated reducing end. Also the anomeric chemical shift at 5.64 ppm arises from a $A_{NS,6S}$ linked to G as shown in Example 1. Signals at 5.20/101.7 ppm and 4.78/72.4 ppm agree with H1 and H5 of $I_{2S}$ residue, and the anomeric signal at 4.6/103.3 ppm with G (Mulloy and Johnson, 1987; Yates et al., 1996). Thus Ui=[$1_4$ ($I_{2S}$); $2_4$ (G)] and Ai=[$5_8$; $5_8$ ($A_{NS,6S}$); $7_8$ (A*)]. In this case we have only one of the two elements of Di' defined =[$-6_{16}$ ($A_{NS,6S}$-G)]. Incorporating the inferences from NMR data as constraints we get $L_{NMR}$=2 sequences: $5_8$ $2_4$ $7_8$ $1_4$ $5_8$ ($A_{NS,6S}$-G-A*-$I_{2S}$-$A_{NS,6S,OMe}$) and $7_8$ $1_4$ $5_8$ $2_4$ $5_8$ (A*-$I_{2S}$-$A_{NS,6S}$-G-$A_{NS,6S,OMe}$)

The disaccharide composition analysis using CE resulted in a single peak corresponding to a trisulfated disaccharide with a shifted migration time indicating the presence of the methylated glucosamine (±Di=[±$D_{16}$]). Using the data from CE one of the sequences from $L_{NMR}$ was eliminated to give the right sequence $5_8$ $2_4$ $7_8$ $1_4$ $5_8$ ($A_{NS,6S}$-G-A*-$I_{2S}$-$A_{NS,6S,OMe}$). This sequence is consistent with the notion that the $A_{NS,6S}$-G linkage is resistant to cleavage by heparinase I, II and III due to the presence of the 3-O sulfated A* (Shriver, Z et al. 2000) thus resulting only in a single disaccharide observed using CE.

Example 3

Decasaccharide (H10)

While the first two synthetic pentasaccharide examples clearly outline the methodology of our approach, the method is better illustrated by the longer and more complex heparin derived oligosaccharide (H10). This sequence is presently among the most complex heparin derived oligosaccharide sequenced to date. It is important to point out that much effort has gone into the isolation and sequencing of H10 (Toida et al., 1996). Due to its complexity, there were inaccuracies in its structure determination in the past and only recently using a combination of analytical tools, this sequence was established (Venkataraman et al., 1999; Shriver et al., 2000). NMR spectroscopy has been used in the past to corroborate its sequence (Shriver et al., 2000) but only the monosaccharide composition was established and there was bias in the interpretation of the NMR data based on the determined sequence. Using these examples we highlight the flexibility of our approach in providing an unbiased assignment of complex heparin derived oligosaccharide structures.

Figure 3A:
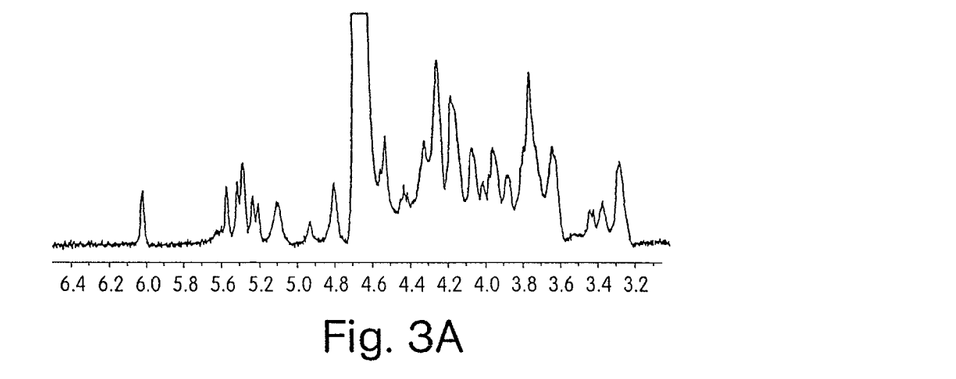
Figure 3B:
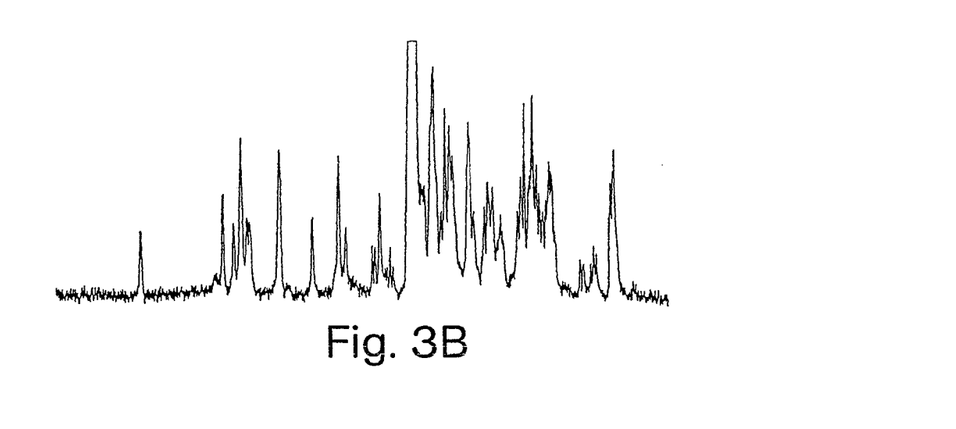

The signal line broadening of the proton spectrum of H10 (FIG. 3A) is caused by the complexation of paramagnetic ions with the negatively charged groups. Addition of EDTA provides a better resolved spectrum (FIG. 3B) by removal of these paramagnetic ions. (Neville, et al., 1989)

The assignment of the anomeric signals (FIG. 3C) and their respective proton patterns (Table 2), were carried out by COSY and TOCSY experiments.

TABLE 2

[1]H chemical shifts of the constituent monosaccharides of the H10 sample. Chemical shifts are given in ppm downfield from trimethylsilyl propionate (TSP) as standard.

|    | ΔU    | $A_{NS,6S}$[a]   | $I_{2S}$[a] | $A_{NS}$ | I     | $A_{NAc}$ | G     | A*    |
|----|-------|------------------|-------------|----------|-------|-----------|-------|-------|
| H1 | 5.521 | 5.42             | 5.20        | 5.369    | 5.019 | 5.386     | 4.668 | 5.460 |
| H2 | 4.635 | 3.31             | 4.34        | 3.275    | 3.767 | 3.940     | 3.415 | 3.483 |
| H3 | 4.314 | 3.65             | 4.22        | 3.65     | 4.126 | 3.77      | 3.71  | 4.571 |
| H4 | 6.001 | 3.77(3.821)[b]   | 4.13        | 3.77     | 4.102 | 3.75      | 3.804 | 4.040 |
| H5 |       | 4.01             | 4.87        | 4.01     | 4.829 | 4.01      | 3.71  | 4.261 |
| H6 |       | 4.40             |             | 4.40     |       | 4.35      |       | nd    |

[a]two monosaccharide residues
[b]H4 chemical shift of the $A_{NS,6S}$ residue following the non reducing ΔU unit.

Figure 3C:
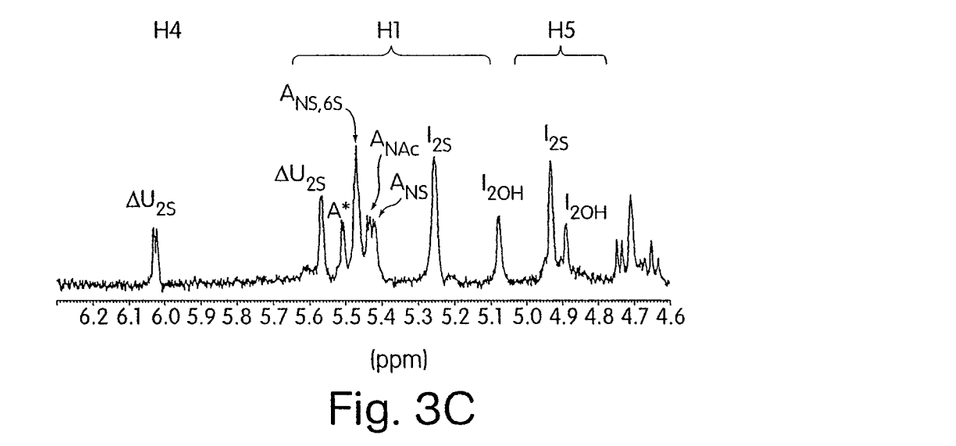

The signals detected between 4.2-4.4 ppm are in agreement with H-6 proton from 6-O sulfated glucosamine. However since this chemical shift lies in the crowded area of the spectrum and due to the presence of minor impurities in the sample it was not possible to accurately determine the molar abundance of glucosamines containing the 6-O sulfate groups. However disaccharide compositional analysis of H10 using CE indicated the presence of 3 major disaccharide components—$\Delta U_{2S}$-$A_{NS,6S}$, $\Delta U$-$A_{NAc, 6S}$, $\Delta U$-A* in the ratio 3:1:1, respectively, giving ±Di=[±D; ±4; ±7]. Thus the data from CE fixed the 6-O sulfation of all the glucosamines.

The relative abundance of the glucosamine monosaccharides calculated by signal integration were $5_8$ ($A_{NS,6S}$): $7_8$ (A*): $4_8$ ($A_{NAc,6S}$)=3:1:1, thus Ai=[$5_8$; $5_8$; $5_8$; $7_8$; $4_8$]. The two α anomeric signals at 5.20 and 5.019 ppm arise from 2-O sulfated and non sulfated iduronic acid, respectively, as demonstrated by the chemical shift pattern. The only β proton signal of the spectrum (at 4.669 ppm) belongs to a glucuronic acid residue. Protons at 6 ppm and 5.521 ppm belong to the H4 and H1 of the ΔU residue. The H2 at 4.635 ppm indicates that the unsaturated uronic acid residue is 2-O-sulfated. The relative abundance of the uronic acid monosaccharides was calculated as $I_{2S}$:I:G: $\Delta U_{2S}$ were identified in the ratio 2:1:1:1 respectively thereby defining Ui=$[1_4; 1_4; 0_4; 2_4; (*1)_4]$ (where * stands for $\Delta U$ since this bit is not defined).

The chemical shift of the signal at 5.369 ppm agrees with a $A_{NS,6S}$ linked to I. The $^1H$ anomeric chemical shift of a $A_{NAc,6S}$ is distinct for $A_{NAc,6S}$-I (5.14-5.18 ppm) and $A_{NAc,6S}$-G (5.30-5.36 ppm) linkages (Cohen, 1999; Chuang, et al., 2001). The anomeric proton of $A_{NAc,6S}$ at 5.386 ppm confirms the presence of $A_{NAc,6X}$-G linkage in the sequence. The chemical shift at 5.42 agrees with both $A_{NS,6S}$ linked to $I_{2S}$ and $A_{NS,6S}$ at the reducing end. Since the $\Delta U$ residue is linked to an $A_{NS,6S}$ unit and a second $A_{NS,6S}$ is linked to I, two possibilities are left for the reducing end, one with $A_{NS,6S}$ and the other with A*. However, the chemical shift pattern associated with A* (H1, 5.464 ppm; H2, 3.480 ppm; H3, 4.564 ppm, H4, 4.041 ppm) is the same as found by Yamada et al (1993) for a heparin tetrasaccharide with this residue at the reducing end (chemical shifts in the Yamada et al paper are systematically shifted about −0.03 ppm with respect to our values). Thus the signal pattern of A* is consistent with its location at the reducing end. Based on the relative abundance of these signals all the elements of Di' were defined as $[-5_{16}; -5_{16}; -4_{16}; -2_{16}]$. Translating the Ai, Ui and Di' to constraints using the PEN framework $L_{NMR}$=12 sequences were obtained (Table 1).

Eliminating the sequences from $L_{NMR}$ that do not contain disaccharide linkages corresponding to ±Di resulted in a single sequence DDD4-7 which is consistent with the H10 sequence obtained earlier (Shriver, et al., 2001).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are herein incorporated by reference.

REFERENCES

Bourin, M.-C., and Lindahl, U. (1993) Glycosaminoglycans and the regulation of blood coagulation. Biochem. J., 289, 313-330.

Breddin, H. K. (2000) Prophylaxis and treatment of deep-vein thrombosis. Semin Thromb Hemost, 26, 47-52.

Casu, B., Guerrini, M., Naggi, A., Torri, G., De-Ambrosi, L., Boveri, G., Gonella, S., Cedro, A., Ferro, L., Lanzarotti, E., Paternò, M., Attolini, M., and Valle, M. G. (1996) Characterization of sulfation patterns of beef and pig mucosal heparins by nuclear magnetic resonance spectroscopy. Arzneim-forsch (Drug Res), 46, 472-477.

Casu, B. and Torri, G. (1999) Structural characterization of low molecular weight heparins. Semin Thromb Hemost, 25, 17-25.

Casu, B. and Lindahl, U. (2001) Structure and biological interactions of heparin and heparan sulfate. Adv. Carbohydr. Chem. Biochem., 57, 159-208.

Chen, Y., Maguire, T., Hileman, R. E., Fromm, J. R., Esko, J. D., Linhardt, R. J. and Marks, R. M. (1997) Dengue virus infectivity depends on envelope protein binding to target cell heparan sulfate [see comments]. Nat Med, 3, 866-871.

Chuang, W. L., Christ, M. D., and Rabenstein, D. L. (2001) Determination of the primary structures of heparin- and heparan sulfate-derived oligosaccharides using band-selective homonuclear-decoupled two-dimensional 1H NMR experiments. Anal Chem, 73, 2310-2316.

Cohen, M. (1999) Low molecular weight heparins in the management of unstable angina/non-Q-wave myocardial infarction. Semin Thromb Hemost, 25, 113-121.

Desai, U. R., and Linhardt, R. J. (1994) Molecular weight of low molecular weight heparins by 13C nuclear magnetic resonance spectroscopy. Carbohydr. Res. 255, 194-198

Fry, E. E., Lea, S. M., Jackson, T., Newman, J. W., Ellard, F. M., Blakemore, W. E., Abu-Ghazaleh, R., Samuel, A., King, A. M., and Stuart, D. I. (1999) The structure and function of a foot-and-mouth disease virus-oligosaccharide receptor complex. Embo J, 18, 543-554.

Guerrini, M., Bisio, A., and Torri, G. (2001) Combined quantitative 1H and 13C-NMR spectroscopy for characterization of heparin preparations. Semin Thromb Hemost, 274, 100-123.

Hricovini, M., Guerrini, M., and Torri, G. (1999) Structure of heparin-derived tetrasaccharide complexed to the plasma protein antithrombin derived from NOEs, J-couplings and chemical shifts. Eur J Biochem, 261, 789-801

Hricovini, M., Guerrini, M., Bisio, A., Torri, G., Petitou, M. and Casu, B. (2001) Conformation of heparin pentasaccharide bound to antithrombin III. Biochem J., 359, 265-272.

Hulett, M. D., Freeman, C., Hamdorf, B. J., Baker, R. T., Harris, M. J., and Parish, C. R. (1999) Cloning of mammalian heparanase, an important enzyme in tumor invasion and metastasis [see comments]. Nat Med, 5, 803-809.

Kay, L. E., Keifer, P., and Saaringen, T. (1992). Pure absorption gradient enhanced heteronuclear single quantum correlation spectroscopy with improved sensitivity. J Am Chem Soc, 114, 10663-10665.

Kreuger, J., Salmivirta, M., Sturiale, L., Giménez-Gallego, G., and Lindahl, U. (2001). Sequence analysis of heparan sulfate epitopes with graded affinities for fibroblast growth factors 1 and 2. J Biol Chem, 276, 30744-30752.

Rosenberg, R. D. (2001). Redesigning heparin. N Engl J Med, 344, 673-675.

Lindahl, U. (2000) Heparin—from anticoagulant drug into the new biology. Glycoconjugate J. 17, 597-605

Linhardt, R. J., and Toida, T. (1999). Capillary Electrophoresis of Oligosaccharides and Complex Carbohydrates. Honda, S. and Thibault, P. (eds), Characterization of Glycosaminoglycans by Capillary Electrophoresis—Humana Press, Inc, pp Liu, D., Shriver, Z., Venkataraman, G., El Shabrawi, Y., and Sasisekharan, R. (2002) Tumor cell surface heparan sulfate as cryptic promoters or inhibitors of tumor growth and metastasis. Proc Natl Acad Sci USA, 99, 568-73.

Mulloy, B. and Johnson, E. A. (1987) Assignment of the 1H-n.m.r. spectra of heparin and heparan sulphate. Carbohydr Res, 170, 151-165.

Neville, G. A., Mori, F., Holme, K. R. and Perlin, A. S. (1989) Monitoring the purity of pharmaceutical heparin preparations by high-field 1H-nuclear magnetic resonance spectroscopy. J Pharm Sci, 78, 101-104.

Petitou, M., Herault, J. P., Bernat, A., Driguez, P. A., Duchaussoy, P., Lormeau, J. C. and Herbert, J. M. (1999) Synthesis of thrombin-inhibiting heparin mimetics without side effects. Nature, 398, 417-422.

Pope, R. M., Raska, C. S., Thorp, S. C. and Liu, J. A (2001) Analysis of heparan sulfate oligosaccharides by nano-electrospray ionization mass spectrometry. Glycobiology, 11, 505-513.

Sasisekharan, R., Ernst, S., and Venkataraman, G. (1997) On the regulation of fibroblast growth factor activity by heparin-like glycosaminoglycans. Angiogenesis, 1, 45-54.

Sasisekharan, R., and Venkataraman, G., (2000) Heparin and heparan sulfate: biosynthesis, structure and function. Curr. Op. in Chem. Biol., 6, 626-631.

Shriver, Z., Liu, D., and Sasisekharan, R. (2002) Emerging views of heparan sulfate glycosaminoglycan structure/activity relationships modulating dynamic biological functions. Trends Cardiovasc Med, 12, 71-77.

Shriver, Z., Raman, R., Venkataraman, G., Drummond, K., Turnbull, J., Toida, T., Linhardt, R., Biemann, K., and Sasisekharan, R. (2000) Sequencing of 3-O sulfate containing heparin decasaccharides with a partial antithrombin III binding site. Proc Natl Acad Sci USA, 97, 10359-10364.

Shriver, Z., Sundaram, M., Venkataraman, G., Fareed, J., Linhardt, R., Biemann, K., and Sasisekharan, R. (2000) Cleavage of the antithrombin III binding site in heparin by heparinases and its implication in the generation of low molecular weight heparin. Proc Natl Acad Sci USA, 97, 10365-70.

Shukla, D., Liu, J., Blaiklock, P., Shworak, N. W., Bai, X., Esko, J. D., Cohen, G. H., Eisenberg, R. J., Rosenberg, R. D., and Spear, P. G. (1999) A novel role for 3-O-sulfated heparan sulfate in herpes simplex virus 1 entry. Cell, 99, 13-22.

Toida, T., Hileman, R. E., Smith, A. E., Vlahova, P. I., and Linhardt, R. J. (1996) Enzymatic preparation of heparin oligosaccharides containing antithrombin III binding sites. J Biol Chem, 271, 32040-32047.

Turnbull, J. E., Hopwood, J. J., and Gallagher, J. T. (1999) A strategy for rapid sequencing of heparan sulfate and heparin saccharides. Proc Natl Acad Sci USA, 96, 2698-2703.

Turpie, G. G., Gallus, A. S., and Hoek, J. A. (2001). A synthetic pentasaccharide for the prevention of deep-vein thrombosis after total hip replacement. N Engl J Med, 344, 619-625.

Venkataraman, G., Shriver, Z., Raman, R., and Sasisekharan, R. (1999) Sequencing complex polysaccharides. Science, 286, 537-542.

Vives, R. R., Pye, D. A., Salmivirta, M., Hopwood, J. J., Lindahl, U., and Gallagher, J. T. (1999) Sequence analysis of heparan sulphate and heparin oligosaccharides. Biochem J, 339, 767-773.

Vlodavsky, I., Friedmann, Y., Elkin, M., Aingorn, H., Atzmon, R., Ishai-Michaeli, R., Bitan, M., Pappo, O., Peretz, T., Michal, I., Spector, L., and Pecker, I. (1999) Mammalian heparanase: gene cloning, expression and function in tumor progression and metastasis [see comments]. Nat Med, 5, 793-802.

Yamada, S., Sakamoto, K., K., Tsuda, H., Yoshida, K., Sugiura, M., and Sugahara, K. (1999) Structural studies of octasaccharides derived from the low-sulfated repeating disaccharide region and octasaccharide serines derived from the protein linkage region of porcine intestinal heparin. Biochemistry, 38, 838-847.

Yamada, S., Yoshida, K., Sugiura, M., Sugahara, K., Khoo, K. H., Morris, H. R., and Dell, A. (1993) Structural studies on the bacterial lyase-resistant tetrasaccharides derived from the antithrombin III-binding site of porcine intestinal heparin. J Biol Chem, 268, 4780-4787.

Yates, E. A., Santini, F., Guerrini, M., Naggi, A., Torri, G., and Casu, B. (1996) 1H and 13C NMR spectral assignments of the major sequences of twelve systematically modified heparin derivatives. Carbohydr Res, 294, 15-27.

We claim:

1. A method of generating a list of possible sequences of an oligosaccharide in a heparin sample comprising:
   providing a heparin sample,
   defining a set of properties of an oligosaccharide in the heparin sample by performing nuclear magnetic resonance (NMR) spectroscopy and another, non-NMR, experimental method, wherein the NMR spectroscopy provides a measurement of one type of disaccharide linkage and the other experimental method provides a measurement of a another type of disaccharide linkage;
   constructing a list of possible oligosaccharides sequences based on the set of properties of the oligosaccharide, to thereby generate a list of possible sequences of the oligosaccharide in the heparin sample.

2. The method of claim 1, wherein the NMR spectroscopy provides a determination of a sulfation pattern of the oligosaccharide.

3. The method of claim 1, wherein the NMR spectroscopy provides a determination of the reducing end and non-reducing end of the oligosaccharide.

4. The method of claim 1, wherein the NMR spectroscopy provides a measure of the monosaccharide composition of the oligosaccharide.

5. The method of claim 1, wherein the NMR is one-dimensional (1D) NMR.

6. The method of claim 1, wherein the NMR is two-dimensional (2D) NMR.

7. The method of claim 6, wherein the 2D NMR is Correlation Spectroscopy (COSY), Total Correlation Spectroscopy (TOCSY), Heteronuclear Single Quantum Correlation (HSQC), Double-Quantum Filtered Correlation Spectroscopy (DQF-COSY), Nuclear Overhauser Effect Spectroscopy (NOESY), Rotating-Frame NOE Spectroscopy (ROESY) or a combination thereof.

8. The method of claim 7, wherein the 2D NMR is COSY, TOCSY, HSQC, ROESY or a combination thereof.

9. The method of claim 1, wherein the NMR is performed on the oligosaccharide in fragmented form.

10. The method of claim 9, wherein the oligosaccharide is fragmented using enzymatic digestion.

11. The method of claim 10, wherein the enzymatic digestion is with a heparinase, a glucuronidase, a sulfatase, or a combination thereof.

12. The method of claim 5, wherein the 1D NMR is performed on the oligosaccharide in fragmented form.

13. The method of claim 12, wherein the oligosaccharide is fragmented using enzymatic digestion.

14. The method of claim 13, wherein the enzymatic digestion is with a heparinase, a glucuronidase, a sulfatase, or a combination thereof.

15. The methods of claim 10, wherein the enzymatic digestion is complete.

16. The method of claim 13, wherein the enzymatic digestion is complete.

17. The method of claim 1, wherein the NMR is performed on the oligosaccharide in its intact form.

18. The method of claim 6, wherein the 2D NMR is performed on the intact oligosaccharide.

19. The method of claim 1, wherein the other experimental method is capillary electrophoresis.

20. The method of claim 19, wherein the capillary electrophoresis is performed on an oligosaccharide in fragmented form.

21. The method of claim 20, wherein the oligosaccharide is fragmented using enzymatic digestion.

22. The method of claim 21, wherein the enzymatic digestion is with a heparinase, a glucuronidase, a sulfatase, or a combination thereof.

23. The method of claim 21, wherein the enzymatic digestion is complete.

24. The method of claim 1, wherein the other experimental method is high performance liquid chromatography.

25. The method of claim 24, wherein the high performance liquid chromatography is performed on an oligosaccharide in fragmented form.

26. The method of claim 25, wherein the oligosaccharide is fragmented using enzymatic digestion.

27. The method of claim 26, wherein the enzymatic digestion is with a heparinase, a glucuronidase, a sulfatase, or a combination thereof.

28. The method of claim 26, wherein the enzymatic digestion is complete.

29. The method of claim 1, wherein the heparin sample is a pig mucosal heparin sample.

30. The method of claim 1, wherein the heparin sample is a low molecular weight heparin sample.

31. The method of claim 1, further comprising a data structure which represents the properties as non-character values.

32. The method of claim 4, further comprising a data structure which represents the properties as non-character values wherein the data structure includes a value for each type of monosaccharide.

33. The method of claim 31, wherein the data structure includes a value for each type of disaccharide linkage.

34. The method of claim 31, wherein the values are binary.

35. The method of claim 11, wherein the heparinase is heparinase I, heparinase II, heparinase III or a combination thereof.

36. The method of claim 14, wherein the heparinase is heparinase I, heparinase II, heparinase III or a combination thereof.

37. The method of claim 22, wherein the heparinase is heparinase I, heparinase II, heparinase III or a combination thereof.

38. The method of claim 27, wherein the heparinase is heparinase I, heparinase II, heparinase III or a combination thereof.

\* \* \* \* \*

UNITED STATES PATENT AND TRADEMARK OFFICE
CERTIFICATE OF CORRECTION

PATENT NO. : 7,737,692 B2  Page 1 of 1
APPLICATION NO. : 12/261000
DATED : June 15, 2010
INVENTOR(S) : Ram Sasisekharan et al.

It is certified that error appears in the above-identified patent and that said Letters Patent is hereby corrected as shown below:

At column 18, claim 1, line 16, delete "of a" and replace with --of--.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,737,692 B2  Page 1 of 1
APPLICATION NO. : 12/261000
DATED : June 15, 2010
INVENTOR(S) : Ram Sasisekharan et al.

It is certified that error appears in the above-identified patent and that said Letters Patent is hereby corrected as shown below:

At column 1, lines 16-19, please delete

"This invention was made with government support under grant numbers GM57073 and CA090940 awarded by The National Institute of Health. The government has certain rights in the invention."

and insert

-- This invention was made with government support under grant numbers R01 CA090940 and R01 GM57073 awarded by the NIH. The government has certain rights in this invention. --

Signed and Sealed this
Twenty-first Day of June, 2011

David J. Kappos
*Director of the United States Patent and Trademark Office*